United States Patent [19]
Nishimoto et al.

[11] Patent Number: 5,824,521
[45] Date of Patent: Oct. 20, 1998

[54] SACCHARIDE COMPOSITION CONTAINING TREHALULOSE, ITS PREPARATION AND USES

[75] Inventors: Tomoyuki Nishimoto; Hiroto Chaen; Shigeharu Fukuda; Toshio Miyake, all of Okayama, Japan

[73] Assignee: Kabushiki Kaisha Hayashibara Seibutsu Kagaku Kenkyujo, Okayama, Japan

[21] Appl. No.: 57,562

[22] Filed: Apr. 9, 1998

Related U.S. Application Data

[62] Division of Ser. No. 811,003, Mar. 4, 1997.

[30] Foreign Application Priority Data

Mar. 4, 1996 [JP] Japan ........................ 8-70913
Mar. 29, 1996 [JP] Japan ........................ 8-99566

[51] Int. Cl.$^6$ ................ C12P 19/12; C12P 19/14; C12P 19/00; C07H 3/04
[52] U.S. Cl. ................ 435/100; 435/72; 435/74; 435/94; 435/97; 435/99; 435/101; 536/123.13
[58] Field of Search ................ 435/100, 99, 94, 435/97, 72, 74, 101; 536/123.13

[56] References Cited

U.S. PATENT DOCUMENTS 4,487,198  12/1984  Miyake et al. .
4,521,252  6/1985  Miyake et al. .
4,948,616  8/1990  Iijima et al. .
5,229,276  7/1993  Sugitani et al. .

FOREIGN PATENT DOCUMENTS 0 636 693   2/1995  European Pat. Off. .
58-23799    2/1983  Japan .
58-72598    4/1983  Japan .
07-170977   7/1995  Japan .

OTHER PUBLICATIONS

Atsuji et al, *J. of Clinical Nutrition*, 41(2):200–208 (1972).
Fujii et al, "Oligosaccharides Produced by Transgucosidation Action of Protaminobacter rubrum alpha–Glucosidase", *Seito–Gijutsu–Kenkyukaishi*, 34:37–44 (1985).
"Enzymic preparation of trehalulose and isomaltulose from sucrose", *Chemical Abstracts*, 117:725, Abstract No. 117:110105e (1992).

*Primary Examiner*—Leon B. Lankford, Jr.
*Assistant Examiner*—Francisco C. Prats
*Attorney, Agent, or Firm*—Browdy and Neimark

[57] ABSTRACT

A saccharide composition containing trehalulose, which is obtainable by allowing a maltose/trehalose converting enzyme to act on a sucrose solution to produce trehalulose, and collecting the resulting trehalulose-containing mixture. Since the enzyme converts sucrose into trehalulose in a relatively high yield and the conversion rate is controllable, a saccharide composition rich in trehalulose is readily obtained on an industrial scale.

9 Claims, No Drawings

SACCHARIDE COMPOSITION CONTAINING TREHALULOSE, ITS PREPARATION AND USES

CROSS-REFERENCE TO RELATED APPLICATIONS

This is a division of copending parent application Ser. No. 08/811,003, filed Mar. 4, 1997.

BACKGROUND OF THE INVENTION

1. Field of the Invention

The present invention relates to a saccharide composition containing trehalulose, its preparation and uses, more particularly, it relates to a saccharide composition containing trehalulose obtained by allowing a maltose/trehalose converting enzyme to act on a sucrose solution to produce trehalulose, a process for producing a saccharide composition comprising a step of allowing a maltose/trehalose converting enzyme to act on a sucrose solution to produce trehalulose, and a composition containing the saccharide composition.

2. Description of the Prior Art

Trehalulose, a disaccharide consisting of glucose and fructose, is a reducing saccharide represented by the chemical formula of 1-O-α-D-glucopyranosyl-D-fructose. In the natural world, honey contains only a minimal amount of trehalulose. Because trehalulose is a non-crystalline saccharide which readily dissolves in water, does not substantially have cariogenicity, and has an about 40% sweetening power of sucrose, it is greatly expected to be used in food products, especially in foods enriched with sweeteners such as jams, "an" (bean jams), and sweet jellies of beans. As is disclosed in "Seito-Gijutsu-Kenkyu-Kaishi, Vol. 34, pp. 37–44 (1985), it is known that trehalulose is produced from sucrose by a method using an α-glucosidase from *Protaminobacter rubrum* with a saccharide-transferring activity. In such an enzymatic reaction, trehalulose is produced as a by-product of crystalline palatinose or 6-O-α-D-glucopyranosyl-D-fructose as a main product. Although it is proposed a method for producing saccharide compositions containing trehalulose which produces trehalulose from sucrose using immobilized cells of *Pseudomonas mesoacidophila* MX-45 as disclosed in Japanese Patent Laid-Open No.169,190/92 or those of *Agrobacterium radiobacter* MX-232 as disclosed in Japanese Patent Laid-Open No.130,886/93, it has not yet been actually used on an industrial scale because of their insufficient enzymatic activity and thermal stability.

SUMMARY OF THE INVENTION

The present invention provides a process for producing trehalulose, which produces trehalulose from sucrose in a satisfactorily high yield and is readily feasible on an industrial scale, and provides a saccharide composition containing trehalulose obtained by the process, and uses thereof.

DETAILED DESCRIPTION OF THE INVENTION

The present inventors energetically studied on processes for producing trehalulose. As a result, they unexpectedly found that the maltose/trehalose converting enzyme, as disclosed in Japanese Patent Laid-Open No.170,977/95 applied by the present inventors, converts maltose into trehalose and readily produces trehalulose from sucrose in a satisfactorily high yield, established a process for producing a saccharide composition containing trehalulose, characterized in that it comprises a step of allowing a maltose/trehalose converting enzyme to act on a sucrose solution, and established a saccharide composition containing trehalulose obtained by the process, and compositions containing the saccharide composition in the form of a food, cosmetic or pharmaceutical. Thus, the present inventors accomplished this invention.

The maltose/trehalose converting enzymes usable in the present invention are intramolecular saccharide-transferring enzymes which are produced by microorganisms of the species Pimelobacter sp. R48 (FERM BP-4315) and *Pseudomonas putida* H262 (FERM BP-4579) as disclosed in Japanese Patent Laid-Open No.170,977/95, and those of the genus Thermus, and convert maltose into trehalose and vice versa. For example, these enzymes have the following physicochemical properties:

(1) Action

Converting maltose into trehalose and vice versa.

(2) Molecular Weight

About 57,000–120,000 daltons on sodium dodecyl sulfate polyacrylamide gel electrophoresis (SDS-PAGE);

(3) Isoelectric Point (pI)

About 3.8–5.1 on isoelectrophoresis using ampholyte;

(4) Inhibition of Activity

Being inhibited by one mM $Cu^{++}$, $Hg^{++}$ and Tris-HCl buffer; and (5) Origin Originated from microorganisms.

The equilibrium point of the reaction system of the maltose/trehalose converting enzymes inclines to the side of trehalose formation, and the trehalose yield increases up to an about 80 w/w % (the wording "w/w %" will be abbreviated as "%" unless specified otherwise) when used maltose as a substrate.

In addition to the above microorganisms, other strains and mutants, which produce such maltose/trehalose converting enzymes and belong to the microorganisms of the genera Pimelobacter, Pseudomonas, and Thermus, can be selectively used. Microorganisms of the genus Thermus such as *Thermus aquaticus* ATCC 25104, *Thermus aquaticus* ATCC 27634, *Thermus aquaticus* ATCC 33923, *Thermus filiformis* ATCC 43280, *Thermus ruber* ATCC 35948, Thermus sp. ATCC 43814, and Thermus sp. ATCC 43815 can be arbitrarily used.

Any synthetic and natural nutrient culture media for culturing the above microorganisms can be used in the present invention as long as the microorganisms can grow therein and produce the maltose/trehalose converting enzymes. The carbon sources used in the present invention include those which are utilized by the microorganisms: For example, saccharides such as glucose, fructose, molasses, trehalose, lactose, sucrose, mannitol, sorbitol, and partial starch hydrolysates, and organic acids such as citric acid and succinic acid, as well as their salts, can be used. The concentration of the carbon sources in nutrient culture media is appropriately selected depending on the type of carbon sources. In the case of using glucose as a carbon source, a preferable concentration is 40 w/v % or lower, especially, a concentration of 10 w/v % or lower is suitably used in view of the growth of microorganisms. Inorganic nitrogen compounds such as ammonium salts and nitrates, and organic nitrogen-containing substances such as urea, corn steep liquor, casein, peptone, yeast extract, and beef extract can be used in the present invention as nitrogen sources. Salts of calcium, magnesium, potassium, sodium, phosphate, manganese, zinc, iron, copper, molybdenum, and cobalt can be selectively used as inorganic ingredients.

The culture conditions for the microorganisms are those under which the microorganisms grow and produce the maltose/trehalose converting enzymes. Usually, the microorganisms are cultured under aerobic conditions at temperatures of about 4°–80° C., preferably, 20°–75° C., and pHs of 5–9, preferably, 6–8.5. Preferable cultivation time is set to those under which the microorganisms can grow, preferably, about 10–100 hours. The concentration of dissolved oxygen (DO) is not specifically restricted to, but usually it is preferably set to about 0.5–20 ppm. The DO is kept within the range by regulating the aeration and stirring ratios, feeding oxygen, and increasing the inner pressure of fermenters. Cultivation methods in a batch-wise and a continuous manner can be used in the present invention.

After completion of the culture of microorganisms, desired enzymes are collected from the culture. Since the activity of maltose/trehalose converting enzyme is found intra- and extra-cellularly, cell-free cultures and cells can be collected as a crude enzyme. Intact cultures can be also used as a crude enzyme. Examples of the methods for separating cultures into cells and cell-free cultures include conventional solid-liquid phase separation methods: For example, centrifugation methods to separate intact cultures, filtration methods comprising a step of adding filtration agents to the cultures or treating intact cultures with precoat filters, and membrane filtration methods using plain filters and hollow fibers. Cell-free cultures can be used as a crude enzyme, preferably, they are concentrated in conventional manner before use: For example, salting out using ammonium sulfate, sedimentation method using acetone and alcohols, and concentration methods using membrane filters such as plain filters and hollow fibers can be used for such purpose.

Intracellular enzymes can be used as a crude enzyme after extracted from cells in conventional manner. Clear crude enzymes can be obtained, for example, by extracting enzymes from cells with disruption methods using ultrasonic or french press or mechanical disruption methods using glass beads and alumina, and by treating the extracts with centrifugation or membrane filtration.

Cell-free cultures, their concentrates, and extracts from cells can be immobilized by conventional manner: For example, binding methods to ion exchangers, covalent bonding and absorption methods to resins and membranes, and inclusion methods using high molecular weight substances can be used. Although the cells separated from cultures can be used as a crude enzyme, the cells can be immobilized to obtain an immobilized enzyme, for example, by mixing the cells with sodium alginate, dropping the mixture into calcium chloride solution to gelatinize to form cell granules, and treating the granules with poly(ethylenimine) and glutaraldehyde.

The crude enzymes can be used without any further treatment or can be purified by conventional manner. For example, an electrophoretically homogeneous enzyme can be obtained by salting out an extract from disrupted cells with ammonium sulfate, concentrating the resultant, dialyzing the concentrate, and subjecting the concentrate successively to anion exchange column chromatography using "DEAE-TOYOPEARL®", hydrophobic column chromatography using "BUTYL-TOYOPEARL®", anion-exchange column chromatography using "MONO Q HR5/5" resin, and gel filtration column chromatography using "TOYOPEARL HW-55".

The activity of maltose/trehalose converting enzymes used in the present invention is assayed as follows: Add one ml of an enzyme solution to one ml of 10 mM phosphate buffer (pH 7.0) containing 20 w/v % maltose as a substrate, react the mixture at 25°, 35° or 60° C. for 60 min, and heat the reaction mixture at 100° C. for 10 min to suspend the enzymatic reaction. Dilute precisely the reaction mixture with 50 mM phosphate buffer (pH 7.5) by 11-fold, add 0.1 ml of a solution containing one unit/ml of trehalase to 0.4 ml of the dilution, incubate the resulting mixture at 45° C. for 120 min, and quantify the glucose content in the mixture using the glucose oxidase method. As a control, use trehalase and an enzyme solution which had been previously inactivated by heating at 100° C. for 10 min, and assay the glucose content similarly as above. With the above assay, determine the content of trehalose produced by the maltose/trehalose converting enzyme based on the increased glucose content. One unit activity of the maltose/trehalose converting enzyme is defined as the amount that forms one $\mu$mole trehalose per minute.

The reaction temperatures for maltose/trehalose converting enzymes from microorganisms of the genera Pimelobacter, Pseudomonas, and Thermus were respectively 25°, 35° and 60° C.

The substrate concentration for the maltose/trehalose converting enzymes used in the present invention is not specifically restricted to. The enzymes react and produce trehalulose even when act on a 0.1 w/v % or 50 w/v % sucrose solution as a substrate. Solutions with a considerably high substrate concentration or with undissolved substrates can be also used in the present invention. Preferable reaction temperatures are, for example, those which do not inactivate the enzymes, particularly, those up to a temperature of about 80° C., preferably, those in the range of about 0°–70° C. More particularly, maltose/trehalose converting enzymes from microorganisms of the genus Thermus more yield trehalulose from sucrose at temperatures of about 30°–50° C. The reaction pHs are usually set to a pH of about 5.5–9.0, preferably, a pH of about 6.0–8.5. The reaction time can be selected while observing the enzymatic reaction conditions, usually, it is selected from about 0.1–200 hours when used about 10–1,000 units/g substrate of a maltose/trehalose converting enzyme, on a dry solid basis (d.s.b.).

It was found that the trehalulose content in the reaction mixtures thus obtained is usually over 10%, preferably, over 30%, and the highest content is about 80%.

The reaction mixtures thus obtained can be subjected to filtration and centrifugation to remove insoluble substances, decolored with an activated charcoal, desalted with ion exchanges in H- and OH-form, and concentrated into syrupy products. The concentrates can be further dried into powdery products, if necessary.

If needs arise, the syrupy and powdery products can be more purified. For example, these products can be readily purified into products with a high purity trehalulose by fractionating on ion-exchange column chromatography, column chromatography using an activated charcoal, and/or column chromatography using a silica gel. Sucrose separated by these column chromatographies can be reused as a substrate for the maltose/trehalose converting enzymes to produce trehalulose.

If necessary, the present saccharide compositions containing trehalulose can be controlled their sweetness and viscosity by hydrolyzing them with an invertase or subjecting them to the action of cyclomaltodextrin glucanotransferase or glucosyltransferase to transfer saccharides thereunto. The saccharide compositions can be further treated with yeast to remove fermentable saccharides. The resulting products can be subjected to the above purification methods such as ion-exchange column chromatography to remove glucose and fructose to obtain high trehalulose content products, followed by purifying and concentrating the products into syrupy products. If necessary, the syrupy products can be arbitrarily dried into powdery products.

The ion-exchange column chromatography used in the present invention includes column chromatography using a strong-acid cation exchange resin as disclosed in Japanese Patent Laid-Open Nos.23,799/83 and 72,598/83 to remove contaminating saccharides to obtain high trehalulose content fractions. In such a column chromatography, fixed-bed, moving-bed, and quasi-moving-bed methods can be selectively used.

The present trehalulose-containing saccharides thus obtained has a relatively high water solubility and a high quality and tastable sweetness. Since trehalulose is hydrolyzed by intestinal hydrolases into glucose and fructose, it is readily assimilated, absorbed, and utilized by living bodies as an energy source when administered orally. Because trehalulose is not substantially fermented by dental carries-inducing microorganisms and inhibitory on the synthesis of insoluble glucans from sucrose by such microorganisms, it can be used as a non-cariogenic sweetener.

As is described above, the present saccharide compositions can be satisfactorily used as a sweetener, taste-improving agent, quality-improving agent, or stabilizer in compositions such as food products, tobaccos, cigarettes, feeds, pet foods, cosmetics, and pharmaceuticals.

The present saccharide compositions can be used intact as a seasoning for sweetening. If necessary, the saccharide compositions can be used together with adequate amounts of one or more other sweeteners, for example, powdered syrup, glucose, maltose, sucrose, isomerized sugar, honey, maple sugar, sorbitol, maltitol, lactitol, dihydrochalcone, stevioside, α-glycosyl stevioside, rebaudioside, glycyrrhizin, L-aspartyl L-phenylalanine methyl ester, saccharin, glycine, and alanine, and/or a filler such as dextrin, starch and lactose.

Because the present saccharide compositions have a taste that well harmonizes with other substances having sourness, acid, saltiness, bitterness, astringency, and deliciousness, and because the compositions have a relatively high acid tolerance and thermal stability, they can be arbitrarily used in food products in general as a sweetener, taste-improving agent, and quality-improving agent.

The saccharide compositions can be used as a seasoning for soy sauce, powdered soy sauce, "miso", "funmatsu-miso" (a powdered miso), "moromi" (a refined sake), "hishio" (a refined soy sauce), "furikake" (a seasoned fish meal), mayonnaise, dressing, vinegar, "sanbai-zu" (a sauce of sugar, soy sauce and vinegar), "funmatsu-sushi-su" (powdered vinegar for sushi), "chuka-no-moto" (an instant mix for Chinese dish), "tentsuyu", (a sauce for Japanese deep-fat fried food), "mentsuyu" (a sauce for Japanese vermicelli), sauce, catsup, "takuan-zuke-no-moto" (an instant mix for Japanese radish), "hakusai-zuke-no-moto" (an instant mix for Chinese cabbage), "yakiniku-no-tare" (a sauce for Japanese grilled meat), curry roux, instant stew mix, instant soup mix, "dashi-no-moto" (an instant stock mix), mixed seasoning, "mirin" (a sweet sake), "shin-mirin" (a synthetic mirin), table sugar, and coffee sugar.

The present saccharide compositions can be also used to sweeten and improve the taste and quality of "wagashi" (Japanese cakes) such as "senbei" (a rice cracker), "arare-mochi" (a rice-cake cube), "okoshi" (a millet-and-rice cake), "mochi" (a rice paste), "manju" (a bun with a bean-jam), "uiro" (a sweet rice jelly), "an" (a bean jam), "yokan" (a sweet jelly of beans), "mizu-yokan" (a soft adzuki-bean jelly), "kingyoku" (a kind of yokan), jelly, pao de Castella and "amedama" (a Japanese toffee); confectioneries such as bun, biscuit, cracker, cookie, pie, pudding, butter cream, custard cream, cream puff, waffle, sponge cake, doughnut, chocolate, chewing gum, caramel and candy; frozen desserts such as ice cream and sherbet; syrups such as "kajitsu-no-syrup-zuke" (a preserved fruit) and "korimitsu" (a sugar syrup for shaved ice); pastes such as flour paste, peanut paste, fruit paste and spread; processed fruits and vegetables such as jam, marmalade, "syrup-zuke" (fruit pickles) and "toka" (conserves); pickles and pickled products such as "fukujin-zuke" (red colored radish pickles), "bettara-zuke" (a kind of whole fresh radish pickles), "senmai-zuke" (a kind of sliced fresh radish pickles) and "rakkyo-zuke" (pickled shallots); meat products such as ham and sausage; products of fish meat such as fish ham, fish sausage, "kamaboko" (a steamed fish paste), "chikuwa" (a kind of fish paste) and "tenpura" (a Japanese deep-fat fried fish paste); "chinmi" (relish) such as "uni-no-shiokara" (salted guts of sea urchin), "ika-no-shiokara" (salted guts of squid), "su-konbu" (processed tangle), "saki-surume" (dried squid strips) and "fugu-no-mirin-boshi" (a dried mirin-seasoned swellfish); "tsukudani" (foods boiled down in soy sauce) such as those of laver, edible wild plants, dried squid, fish, and shellfish; daily dishes such as "nimame" (cooked beans), potato salad and "konbu-maki" (a tangle roll); milk products; canned and bottled products such as those of meat, fish meat, fruit and vegetable; alcoholic beverages such as sake, synthetic sake, wine, and liquors; soft drinks such as coffee, tea, cocoa, juice, carbonated beverage, sour milk beverage and beverage containing lactic acid bacteria; instant food products such as instant pudding mix, instant hot cake mix and "sokuseki-shiruko" (an instant mix of adzuki-bean soup with rice cake) and instant soup mix; and beverages such as baby foods, foods for therapy, and beverages supplemented with nutrition.

The present saccharide compositions can be further used in feeds and pet foods for animals such as domestic animals, poultry, silk worms, and fishes to improve their taste preferences and improve the growth of animals. These compositions can be arbitrarily used as a sweetener, taste-improving agent, masking agent, or quality-improving agent in other products including tobacco, cigarette, cosmetics, and pharmaceuticals in a solid, paste or liquid form such as a dentifrice, lipstick, rouge, chapped lip, internal medicine, tablet, troche, cod liver oil in a drop form, cachou, oral refrigerant, and gargle.

The methods to incorporate the present saccharide compositions into the above compositions include conventional methods, for example, mixing, kneading, dissolving, melting, soaking, permeating, sprinkling, applying, coating, spraying, injecting, crystallizing, and solidifying. The saccharide compositions are generally incorporated into the above compositions in an amount of 0.1% or more, preferably, 1% or more of trehalulose, d.s.b. The followings describe the present invention in more detail:

Experiment 1

Production of Enzyme

A liquid nutrient culture medium, consisting of 0.5 w/v % polypeptone, 0.1 w/v % yeast extract, 0.07 w/v % sodium nitrate, 0.01 w/v % disodium hydrogenphosphate, 0.01 w/v % magnesium sulfate, and water, was adjusted to pH 7.5. One hundred ml aliquots of the culture medium were placed in 500-ml Erlenmeyer flasks which were then autoclaved at 120° C. for 20 min, cooled, and inoculated with a stock culture of *Thermus aquaticus* ATCC 33923, followed by incubating at 60° C. for 24 hours under shaking conditions of 200 rpm to obtain a culture for a seed culture.

About 20 L aliquots of a fresh preparation of the same liquid nutrient culture medium as used in the above were placed in two 30-L fermenters, sterilized by heating, cooled to 60° C., and inoculated with one v/v % of the seed culture, followed by the incubation at 60° C. and pH 6.5–8.0 for about 20 hours under agitation-aeration conditions.

Experiment 2

Purification of Enzyme

The culture obtained in Experiment 1 was centrifuged to obtain about 0.28 kg of wet cells, and the cells were suspended in 10 mM phosphate buffer (pH 7.0). About 1.9 L of the cell suspension was treated with "MODEL US300", an ultrasonic disintegrator commercialized by Nihonseiki Kaisha, Ltd., Tokyo, Japan, to disrupt cells. The resulting mixture was centrifuged at 15,000 G for 30 min to obtain an about 1.8 L of a supernatant. Ammonium sulfate was added to and dissolved in the supernatant to give a saturation degree of 0.7, allowed to stand at 4° C. overnight to form a precipitate, and centrifuged to collect the precipitate.

The precipitate was dissolved in 10 mM phosphate buffer (pH 7.0), dialyzed against a fresh preparation of the same buffer for 24 hours, and centrifuged to remove insoluble substances. 1,560 ml of the dialyzed solution was divided into 3 portions which were then separately subjected to ion-exchange column chromatography using 530 ml of "DEAE-TOYOPEARL 650", a gel commercialized by Tosoh Corporation, Tokyo, Japan.

A maltose/trehalose converting enzyme was adsorbed on the gel and eluted from the column with a fresh preparation of the same buffer containing salt. The eluate with an enzyme activity was collected and pooled, and the solution was fed to hydrophobic column chromatography using a column packed with 380 ml of "BUTYL-TOYOPEARL® 650", a gel commercialized by Tosoh Corporation, Tokyo, Japan. The maltose/trehalose converting enzyme adsorbed on the gel was eluted from the column with a linear gradient solution containing ammonium sulfate decreasing from 1 to 0M, followed by collecting fractions with the enzyme activity.

The fractions were pooled and subjected to gel filtration chromatography using 380 ml of "TOYOPEARL® HW-55S", a gel commercialized by Tosoh Corporation, Tokyo, Japan, followed by collecting fractions with the enzyme activity.

The fractions were pooled and subjected to ion-exchange column chromatography using 1.0 ml of "MONO Q HR5/5", a gel commercialized by Pharmacia LKB Biotechnology AB, Uppsala, Sweden, followed by feeding to the column with a linear gradient solution of salt increasing from 0.1 to 0.35M and collecting fractions with the enzyme activity. Thus a maltose/trehalose converting enzyme with an electrophoretically single protein band was obtained. The specific activity of the enzyme was 135 units/mg protein.

Experiment 3

Action on Saccharides

Fifty units/g saccharide, d.s.b., of a maltose/trehalose converting enzyme was allowed to act on saccharides to check whether the saccharides can be used as substrates for the enzyme. For such a purpose, glucose, maltose, maltotriose, maltotetraose, trehalose, neotrehalose, kojibiose, isomaltose, maltitol, cellobiose, gentiobiose, sucrose, trehalulose, turanose, maltulose, palatinose, or lactose was prepared into a solution with a final concentration of 5 w/v %.

To each solution was added 50 units/g substrate, d.s.b., of an enzyme obtained by the method in Experiment 2, and subjected to an enzymatic reaction at 50° C. and pH 7.0 for 48 hours. The reaction mixtures before and after the enzymatic reaction were sampled to check whether the enzyme acts on the saccharides by allocating the samples on plates for thin layer chromatography (hereinafter abbreviated as "TLC") using "KIESEL GEL 60", an aluminum plate, 20×20 cm, commercialized by Merck & Co., Inc., N.J., USA. In the TLC a solvent system of 1-butanol, pyridine, and water (=6:4:1 by volume) was used, and each sample was developed once. The coloration was effected by spraying to the plates 20 v/v % sulfuric acid in methanol, and heating the plates at 110° C. for 10 min. Reaction mixtures, in which enzymatic products were detected, were analyzed for saccharide composition on gas chromatography (hereinafter abbreviated as "GLC"). The reaction mixtures were sampled, dried, dissolved in pyridine, and trimethylsilylated after formed into oximes, and the resulting products were used for analysis. The gas chromatograph and conditions used in this experiment were "GC-16A" commercialized by Shimadzu Corporation, Tokyo, Japan; a stainless steel column, 3 mm in diameter and 2 m long, packed with 2% "OV-17/CHROMOSOLVE W", a column commercialized by GL Sciences Inc., Tokyo, Japan; flow rate of nitrogen gas as a carrier gas, 40 ml/min; column oven temperature, 160°–320° C.; increasing rate of temperature, 7.5° C./min; and detector, a hydrogen flame ionization detector. The results were in Table 1.

TABLE 1

| Substrate | Action of enzyme | Substrate | Action of enzyme |
| --- | --- | --- | --- |
| Glucose | – | Maltitol | – |
| Maltose | +++ | Cellobiose | – |
| Maltotriose | – | Gentiobiose | – |
| Maltotetraose | – | Sucrose | ++ |
| Trehalose | ++ | Trehalulose | + |
| Neotrehalose | + | Turanose | + |
| Kojibiose | – | Maltulose | + |
| Nigerose | – | Palatinose | + |
| Isomaltose | – | Lactose | – |

Note: In the columns of "Action of enzyme", the symbol "–" means unchanged before and after the enzymatic reaction; "+", the substrate was reduced and the product yield was less than 25%; "++", the substrate was reduced and the product yield was at least 25% but less than 75%; and "+++", the substrate was reduced and the product yield was at least 75%.

As is evident from the results in Table 1, it was unexpectedly revealed that the maltose/trehalose converting enzyme used in the present invention acts on maltose and trehalose, as well as neotrehalose, sucrose, trehalulose, turanose, maltulose and palatinose, especially, on sucrose among the saccharides tested.

Experiment 4

Enzymatic Reaction Product

Experiment 4-1

Product from Sucrose

One hundred units/g substrate, d.s.b., of a maltose/trehalose converting enzyme, obtained by the method in Experiment 2, was added to an aqueous sucrose solution with a final concentration of 10 w/v %, and the mixture was subjected to an enzymatic reaction at 50° C. and pH 6.5 for 48 hours. The composition of the reaction mixture was analyzed on GLC similarly as in Experiment 3. To identify the reality, trimethylsilylated derivatives having not been formed into oximes were also used as samples for analysis. The results were in Table 2.

TABLE 2

| Saccharide | GLC retention time (min) | | Saccharide composition (%) |
|---|---|---|---|
| | Trimethylsilylated derivative | Trimethylsilylated derivative after formed into oxime | |
| A Fructose | 2.9 and 3.9 | 4.2 | 5.7 |
| Glucose | 4.0 and 4.8 | 4.8 | 6.0 |
| Sucrose | 11.6 | 11.6 | 12.3 |
| X | 12.5 and 12.7 | 13.7 | 73.4 |
| Other disaccharides | — | — | 2.6 |
| B Trehalulose | 12.5 and 12.7 | 13.7 | — |

Note: In the Table, the symbols "A" and "B" mean "Reaction mixture" and "Standard saccharide", respectively.

As is evident from the results in Table 2, it was found that an unknown substance "X" was formed in quantity from sucrose, and the retention times of trimethylsilylated derivative of the substance "X" before and after formed into oxime coincided with those of trehalulose. To identify the substance "X", the following confirmation tests were conducted using a high purity saccharide powder containing trehalulose prepared in Experiment 8:

(1) Constituent Saccharide

GLC analysis of the products, which was formed after hydrolysis of the substance "X" with 0.5N-sulfuric acid, detected glucose and fructose in a molar ratio of 1:0.83 other than intact substance "X". Considering the stability of hexose and ketose to acids, it can be judged that the substance "X" consists of equimolar glucose and fructose.

(2) Hydrolysis by Enzyme

Not hydrolyzed by an invertase from yeast. Hydrolyzed by α-glucosidase from yeast into glucose and fructose in a molar ratio of 1:1.

(3) Mass 342 on FD-MS analysis.

(4) Specific Rotatory Power

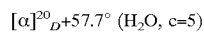

$[\alpha]^{20}_D + 57.7°$ (H$_2$O, c=5)

For a standard trehalulose:

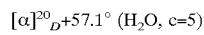

$[\alpha]^{20}_D + 57.1°$ (H$_2$O, c=5)

Based on the facts that the substance "X" is a disaccharide consisting of glucose and fructose and the other properties thereof coincided with those of a standard trehalulose, it can be judged that the substance is trehalulose, 1-O-α-D-glucopyranosyl-D-fructose. Comparison of the retention times with those of the standard preparations on GLC analysis revealed that other minor components, formed from sucrose after hydrolysis with the maltose/trehalose converting enzyme, were palatinose and turanose.

As is evident from these results, the maltose/trehalose converting enzyme converts maltose into trehalose and vice versa, and converts sucrose into trehalulose. The enzyme did not substantially convert trehalulose into sucrose.

Experiment 4-2

Sugar Composition of Product from Sucrose

About 330 units/g of a purified maltose/trehalose converting enzyme, obtained by the method in Experiment 2, was added to an aqueous sucrose solution with a final concentration of 10 w/v %, and the mixture was enzymatically reacted at 40°–70° C. and pH 6.5 for 30 min. Thereafter, the sugar composition of the reaction mixture was analyzed on GLC similarly as in Experiment 3. The results were in Table 3.

TABLE 3

| Temperature (°C.) | Sugar composition (%) | | | | | |
|---|---|---|---|---|---|---|
| | Fructose | Glucose | Sucrose | Trehalulose | Turanose | Palatinose |
| 40 | 3.4 | 3.9 | 7.8 | 81.0 | 1.3 | 2.6 |
| 45 | 5.5 | 5.7 | 5.2 | 78.8 | 1.6 | 3.2 |
| 50 | 8.2 | 8.9 | 3.7 | 73.7 | 1.8 | 3.7 |
| 55 | 11.7 | 12.4 | 3.0 | 67.6 | 1.7 | 3.6 |
| 60 | 15.3 | 16.2 | 2.9 | 59.6 | 2.0 | 4.0 |
| 65 | 19.6 | 19.3 | 3.8 | 51.8 | 1.8 | 3.7 |
| 70 | 21.3 | 21.1 | 7.7 | 45.7 | 1.4 | 2.8 |

As is evident from the results in Table 3, the maltose/trehalose converting enzyme used in the present invention formed a saccharide composition containing about 45–80% trehalulose, d.s.b. The trehalulose yield increased as the temperature decreased, while the yield decreased as the temperature increased. The enzyme is characteristic in that it gives a higher ratio of trehalose to palatinose, i.e. the ratio of trehalulose/palatinose is 14 or higher, and it produces saccharide compositions containing trehalulose with only a palatinose content of 4% or lower, d.s.b. The present saccharide composition, containing trehalulose produced with the enzyme, clearly defers from conventional saccharide compositions, containing trehalulose produced with conventional enzymes, on the ratio of trehalulose/palatinose and the palatinose content.

Experiment 5

Influence of Enzyme Amount on Trehalulose Formation

To a 10% sucrose solution was added 2, 5, 10, 20, 50, 100 or 200 units/g sucrose, d.s.b., of a purified maltose/trehalose converting enzyme obtained by the method in Experiment 2, and the mixture was allowed to react enzymatically at 40° C. and pH 6.5 while sampling the reaction mixture at a prescribed time interval. The samples were heated at 100° C. for 10 min to inactivate the remaining enzyme and analyzed on GLC similarly as in Experiment 3. The amount of enzyme used and the trehalulose content in the reaction mixture at each reaction time were in Table 4.

TABLE 4

| Reaction time | Trehalulose yield (%) Amount of enzyme (unit/g sucrose) | | | | | | |
| --- | --- | --- | --- | --- | --- | --- | --- |
| (min) | 2 | 5 | 10 | 20 | 50 | 100 | 200 |
| 24 | 0.3 | 1.5 | 6.2 | 14.3 | 40.3 | 58.0 | 72.3 |
| 48 | 0.6 | 3.0 | 11.1 | 23.5 | 56.5 | 72.3 | 80.9 |
| 72 | 0.9 | 4.4 | 15.4 | 30.7 | 65.2 | 78.8 | 79.2 |
| 96 | 1.1 | 5.8 | 19.2 | 36.2 | 70.5 | 81.0 | 78.6 |

As is evident from the results in Table 4, it was found that 10 units/g sucrose, d.s.b., of the enzyme produced trehalulose in a yield of 10% or more, and 100 units/g sucrose or more of the enzyme more produced trehalulose in a yield of 80% or more. It can be estimated that even 10 units/g sucrose, d.s.b., of the enzyme will produce trehalulose in a yield of 30% or more, if only the enzyme is allowed to act on the substrate for a longer time.

Experiment 6

Influence of Sucrose Concentration on Trehalulose Formation

One hundred units/g sucrose, d.s.b., of a purified maltose/trehalose converting enzyme, obtained by the method in Experiment 2, was allowed to act on a solution containing 2.5%, 5%, 10%, 20% or 40% sucrose, and the mixture was allowed to react enzymatically at 40° C. and pH 6.5 for 96 hours and heated at 100° C. for 10 min to inactivate the remaining enzyme. The saccharide composition of each reaction mixture was analyzed on GLC similarly as in Experiment 3. The results were in Table 5.

TABLE 5

| Sucrose concentration | Saccharide composition (%) | | | |
| --- | --- | --- | --- | --- |
| (%) | Monosaccharide | sucrose | Trehalulose | Others |
| 2.5 | 4.5 | 18.7 | 74.5 | 2.3 |
| 5.0 | 4.9 | 14.8 | 77.7 | 2.6 |
| 10.0 | 5.8 | 11.4 | 79.5 | 3.3 |
| 20.0 | 6.5 | 9.8 | 79.5 | 4.2 |
| 40.0 | 8.0 | 7.3 | 79.3 | 5.4 |

As is evident from the results in Table 5, the trehalulose yield from sucrose was 70% or more even with a 2.5% sucrose solution. The more the sucrose concentration, the more the enzymatic reaction proceeds. The trehalulose yield was about 80% when the enzyme was allowed to act on 10% or more of sucrose solutions.

Experiment 7

Influence of Temperature on Trehalulose Formation

A 10% sucrose solution was adjusted to pH 6.5, admixed with 100 units/g sucrose, d.s.b., of a purified maltose/trehalulose converting enzyme obtained by the method in Experiment 2, and the mixture was allowed to react enzymatically at 20°, 30°, 40°, 50° or 60° C. while sampling the reaction mixture at a prescribed time interval. The samples were heated at 100° C. for 10 min to inactivate the remaining enzyme. The saccharide composition of each reaction mixture was analyzed on GLC similarly as in Experiment 3. The trehalulose content in each reaction mixture at different reaction times and temperatures was in Table 6.

TABLE 6

| Reaction time | Trehalulose yield (%) | | | | |
| --- | --- | --- | --- | --- | --- |
| (hour) | 20° C. | 30° C. | 40° C. | 50° C. | 60° C. |
| 8 | 10.8 | 21.7 | 33.4 | 41.4 | 43.4 |
| 24 | 23.6 | 42.4 | 57.9 | 64.1 | 59.3 |
| 48 | 35.0 | 56.0 | 72.4 | 73.4 | 63.2 |
| 72 | 49.3 | 67.0 | 78.7 | 74.6 | 62.4 |
| 96 | 60.3 | 73.2 | 81.0 | 73.7 | 59.6 |

As is evident from the results in Table 6, the enzyme produced trehalulose in a high yield of about 70% or more when reacting at about 30°–50° C.

Experiment 8

Preparation of Trehalulose from Sucrose

Ten parts by weight of sucrose was dissolved in 40 parts by weight of water, and admixed with 100 units/g sucrose, d.s.b., of a purified maltose/trehalose converting enzyme obtained by the method in Experiment 2, followed by the enzymatic reaction at 40° C. and pH 6.5 for 90 hours. Thereafter, the reaction mixture was heated at 100° C. for 10 min to inactivate the remaining enzyme and cooled to 40° C. To decompose the remaining sucrose, the reaction mixture was adjusted to pH 4.0, admixed with 20 units/g saccharides, d.s.b., of an invertase from yeast, followed by the enzymatic reaction at 40° C. for 24 hours and the incubation at 100° C. for 10 min to inactivate the remaining enzyme. The mixture thus obtained contained about 80% trehalulose, d.s.b. The mixture was decolored with an activated charcoal, desalted and purified on ion exchangers in H- and OH-form, and concentrated into an about 50% saccharide solution for a material saccharide solution. To increase the trehalulose content, the saccharide solution was subjected to ion-exchange column chromatography using 4 jacketed stainless steel columns, 5.4 cm in diameter, cascaded in series to give a total gel-bed depth of 20 m, packed with "DOWEX 50WX4 ($Ca^{++}$-form)", a strong-acid cation exchange resin commercialized by Dow Chemical Company, Midland, Mich., USA.

Five v/v % of the saccharide solution was added to the resin while keeping the inner column temperature at 40° C., followed by fractionating the saccharide solution to remove coexisting saccharides such as fructose and glucose by feeding to the column hot water heated to 40° C. at an SV (space velocity) 0.2 and collecting high trehalulose content fractions. The fractions were pooled, purified, concentrated, dried in vacuo, and pulverized to obtain a saccharide powder rich in trehalulose with a purity of 98% in a yield of about 70%, d.s.b.

Experiment 9

Production of Trehalulose from Sucrose by Maltose/Trehalose Converting Enzyme from Other Microorganism According to the method in Experiments 1 and 2, maltose/trehalose converting enzymes from Pimelobacter sp. R48 (FERM BP-4315) and *Pseudomonas putida* H262 (FERM BP-4579), and those from *Thermus aquaticus* ATCC 27634,

*Thermus ruber* ATCC 35948, Thermus sp. ATCC 43815, and *Thermus aquaticus* ATCC 33923 were partially purified on column chromatography using "DEAE-TOYOPEARL 650". Under the conditions in Table 7, each enzyme was allowed to react on a 20% sucrose solution for 96 hours, and the saccharide composition of the reaction mixture was analyzed on GLC. The trehalulose yield from sucrose for each enzyme was in Table 7.

TABLE 7

| Microorganism | Amount of enzyme (unit/g sucrose) | Reaction temperature (°C.) | Reaction pH | Trehalulose yield (%) |
|---|---|---|---|---|
| Pimelobacter sp. R48 | 30 | 15 | 7.0 | 75.2 |
| *Pseudomonas putida* H262 | 30 | 25 | 7.0 | 70.2 |
| *Thermus aquaticus* ATCC 27634 | 50 | 50 | 6.5 | 71.6 |
| *Thermus ruber* ATCC 35948 | 50 | 40 | 6.5 | 72.3 |
| Thermus sp. ATCC 43815 | 50 | 50 | 6.5 | 70.2 |
| *Thermus aquaticus* ATCC 33923 | 50 | 50 | 6.5 | 73.4 |

It was revealed that all the enzymes from the above microorganisms produced trehalulose from sucrose in a yield of over 70%.

Experiment 10

Utilization Test In Vivo

In accordance with the method as reported by H. Atsuji et al. in "*Journal of Clinical Nutrition*", Vol.41, No.2, pp.200–208 (1972), 30 g of the saccharide powder rich in trehalulose with a purity of 98%, d.s.b., in Experiment 8 was prepared into a 20 w/v % aqueous solution which was then orally administered to 3 healthy male volunteers of 25-, 27- and 30-year-old, and their blood were sampled at a pre-scribed time interval, followed by assaying the blood sugar- and insulin-levels. As a control glucose was used. As a result, the blood sugar- and insulin-levels were about half levels of those of glucose in the volunteers administered with trehalulose, and showed the highest level at an about 0.5–1 hour after the administration. Based on the fact that trehalulose consists of glucose and fructose in a molar ratio of 1:1, it is judged that the saccharide tested is readily assimilated, absorbed, and utilized as an energy source.

Experiment 11

Acute Toxicity Test

By using dd-strain mice, 7-week-old, the saccharide powder rich in trehalulose with a purity of 98%, d.s.b., prepared in Experiment 8 was orally administered to the mice for acute toxicity test. No mouse died up to a dose of 15 g/kg mouse by weight and a higher dose test was impossible. Thus the toxicity of the saccharide is extremely low.

Examples for reference, Examples A, and Examples B describe the preparation of maltose/trehalose converting enzymes used in the present invention, the present saccharide compositions containing trehalulose prepared by the enzymes, and the present compositions containing the saccharide compositions:

Example for Reference 1

A seed culture of Pimelobacter sp. R48 (FERM BP-4315) was inoculated into a liquid nutrient culture medium consisting of 4.0 w/v % glucose, 0.5 w/v % polypeptone, 0.1 w/v % yeast extract, 0.1 w/v % dipotassium hydrogenphosphate, 0.06 w/v % sodium dihydrogenphosphate, 0.05 w/v % magnesium sulfate heptahydrate, 0.5 w/v % calcium carbonate, and water, and incubated in a fermenter for about 60 hours under aeration-agitation conditions similarly as in Experiment 1 except for the incubation temperature was set to 27° C. An about 18 L of the resulting culture was treated with "MINI-RABO", a super-pressure cell disrupting apparatus commercialized by Dainippon Pharmaceutical Co., Ltd., Tokyo, Japan, to disrupt cells, and the mixture was centrifuged to obtain a supernatant. Thereafter, the supernatant was concentrated using a UF membrane to obtain a 300 ml of enzyme concentrate containing about 30 units/ml of a maltose/trehalose converting enzyme.

Example for Reference 2

A seed culture of *Pseudomonas putida* H262 (FERM BP-4579) was inoculated into a liquid nutrient culture medium consisting of 2.0 w/v % glucose, 1.0 w/v % ammonium sulfate, 0.1 w/v % dipotassium hydrogenphosphate, 0.06 w/v % sodium dihydrogenphosphate, 0.05 w/v % magnesium sulfate heptahydrate, 0.3 w/v % calcium carbonate, and water, and incubated in a fermenter for about 20 hours under aeration-agitation conditions similarly as in Experiment 1 except for the incubation temperature was set to 27° C. An about 18 L of the resulting culture was centrifuged to obtain an about 0.4 kg wet cells which were then suspended in 4 L of 10 mM phosphate buffer, treated with an ultrasonic disintegrator to disrupt cells. The cell suspension was centrifuged to obtain a supernatant which was then concentrated with a UF membrane to obtain an about 100 ml of enzyme concentrate containing about 15 units/ml of a maltose/trehalose converting enzyme.

Example for Reference 3

In accordance with the method in Experiment 1, *Thermus aquaticus* ATCC 33923 was cultured for about 20 hours under aeration-agitation conditions. 0.18 kg of wet cells, collected from an about 18 L of the culture, was suspended in 10 mM phosphate buffer (pH 7.0) and treated with an ultrasonic disintegrator to disrupt cells. The resulting mixture was centrifuged to obtain a supernatant which was then concentrated with a UF membrane to obtain an about 100 ml of enzyme concentrate containing about 50 units/ml of a maltose/trehalose converting enzyme.

Example A-1

Sucrose was prepared into a solution with a final sucrose concentration of 30 w/v %, and 25 units/g dry solid of a maltose/trehalose converting enzyme obtained by the method in Example for reference 1, followed by incubating the mixture at 10° C. and pH 7.0 for 150 hours. The reaction mixture was heated at 95° C. for 10 min, collected, and, in conventional manner, decolored and filtered with an activated charcoal, desalted and purified on ion exchangers in H- and OH-form, and concentrated into an about 75% trehalulose syrup in a yield of about 95%, d.s.b. The syrup contained about 75% trehalulose, d.s.b. Since the syrup has a high-quality sweetness, adequate viscosity, and satisfactory humectancy, it can be used as a sweetener, quality-improving agent or stabilizer in food products, cosmetics, and pharmaceuticals. The syrup can be used after hydrogenating reducing trehalulose and other saccharides in the syrup into their corresponding sugar alcohols.

Example A-2

Sucrose was prepared into a solution with a final sucrose concentration of 20 w/v %, and 20 units/g dry solid, d.s.b., of a maltose/trehalose converting enzyme obtained by the method in Example for reference 2, followed by incubating the mixture at 25° C. and pH 7.0 for 120 hours. The reaction mixture was heated at 95° C. for 10 min, collected, and, in conventional manner, decolored and filtered with an activated charcoal, desalted and purified on ion exchangers in H- and OH-form, concentrated, dried in vacuo, and pulverized into a trehalulose syrup in a yield of about 90%, d.s.b. The syrup contained about 70% trehalulose, d.s.b. Since the syrup has a high-quality sweetness, it can be used as a sweetener, quality-improving agent, stabilizer, filler or excipient in food products, cosmetics, and pharmaceuticals.

Example A-3

A reaction mixture, obtained by an enzymatic reaction using a maltose/trehalose converting enzyme prepared by the method in Example A-1, was adjusted to pH 4.5, and admixed with 5 units/g dry solid of invertase, followed by the enzymatic reaction at 40° C. for 24 hours. The reaction mixture thus obtained was incubated at 95° C. for 10 min, cooled, decolored and filtered with an activated charcoal in conventional manner, desalted and purified on ion exchangers in H- and OH-form, and concentrated into an about 55% saccharide solution. As a material saccharide solution, the saccharide solution was subjected to column chromatography using "DOWEX 99 ($Ca^{++}$-form, polymerization degree of 6%)", a strong-acid cation exchange resin commercialized by Dow Chemical Company, Midland, Mich., USA, similarly as in Experiment 8 to collect fractions rich in trehalulose. The fractions were pooled, purified, and concentrated to obtain a high trehalose content syrup containing about 75% trehalulose in a yield of about 60%, d.s.b. Since the syrup contains about 95% trehalulose, d.s.b., and has a high-quality sweetness, adequate viscosity, and satisfactory humectancy, it can be arbitrarily used as a sweetener, quality-improving agent or stabilizer in food products, cosmetics, and pharmaceuticals.

Example A-4

Sucrose was prepared into a solution with a final sucrose concentration of 40 w/v %. The sucrose solution was mixed with 50 units/g dry solid of a maltose/trehalose converting enzyme obtained by the method in Example for reference 3, and enzymatically reacted at 40° C. and pH 6.5 for 96 hours. The reaction mixture was adjusted to pH 4.5, admixed with 5 units/g dry solid of invertase, and enzymatically reacted at 40° C. for 24 hours. After keeping at 95° C. for 10 min the reaction mixture was cooled, decolored and filtered with an activated charcoal, desalted and purified on ion exchangers in H- and OH-form, and concentrated into an about 55% saccharide solution. As a material saccharide solution, the saccharide solution was subjected to column chromatography using "DOWEX 99 ($Ca^{++}$-form, polymerization degree of 6%)", a strong-acid cation exchange resin commercialized by Dow Chemical Company, Midland, Mich., USA, similarly as in Experiment 8 to collect fractions rich in trehalulose. The fractions were pooled, purified, concentrated, and spray dried to obtain a high trehalulose content powder in a yield of about 60%, d.s.b. Since the syrup contains about 95% trehalulose, d.s.b., and has a high-quality sweetness, adequate viscosity, and satisfactory humectancy, it can be arbitrarily used as a sweetener, quality-improving agent or stabilizer in food products, cosmetics, and pharmaceuticals.

Example B-1

Sweetener

One part by weight of a high trehalulose content powder, obtained by the method in Example A-4, was mixed to homogeneity with 0.05 part by weight of "α-G SWEET", α-glycosylstevioside commercialized by Toyo Sugar Refining Co., Ltd., Tokyo, Japan, and the mixture was fed to a granulator to obtain a granule of sweetener. The product has a high quality sweetness, an about 2-fold higher sweetening power or sucrose, and an about half calorific value of sucrose per sweetening power. The product can be advantageously used as a low-caloric sweetener to sweeten calorie-sparing foods for fat persons and diabetics who are restricted to reducing calorie intake. Because dental-carries inducing microorganisms less form acids and insoluble glucans when assimilate the product, it can be satisfactorily used to sweeten food products to prevent dental carries.

Example B-2

Hard Candy

To 100 parts by weight of a 55% sucrose solution was mixed by heating with 30 parts by weight of a trehalulose syrup obtained by the method in Example A-1, then concentrated by heating to render a moisture content of less than 2% under a reduced pressure, mixed with one part by weight of citric acid and adequate amounts of a lemon flavor and a coloring agent. The mixture was shaped in conventional manner into a desired product. The product is a high-quality hard candy having insubstantial crystallization of sucrose and a satisfactory biting property and taste.

Example B-3

Strawberry Jam

One hundred and fifty parts by weight of fresh strawberry, 20 parts by weight of maltose, 40 parts by weight of a trehalulose syrup obtained by the method in Example A-1, 5 parts by weight of pectin, and one part by weight of citric acid were mixed, and the mixture was boiled up in a plain vessel, and bottled to obtain a desired product which is a tastable and well-colored strawberry jam.

Example B-4

Lactic Acid Beverage

Ten parts by weight of skim milk was sterilized by heating at 80° C. for 20 min, cooled to 40° C., inoculated with 0.3 part by weight of a starter, and fermented at about 37° C. for 10 hours. Thereafter, the fermented mixture was homogenized, mixed with 4 parts by weight of a trehalulose-containing saccharide powder obtained by the method in Example A-2, one part by weight of sucrose, and 2 parts by weight of an isomerized sugar syrup, and sterilized by heating at 70° C. The mixture thus obtained was cooled, admixed with an adequate amount of a flavor, and bottled to obtain a desired product which is a high-quality lactic acid beverage having an acidity well-harmonized with taste and sweetness.

Example B-5

Sweetened Condensed-Milk

To 100 parts by weight of a fresh milk were added 3 parts by weight of a high trehalulose content syrup obtained by the method in Example A-3, and one part by weight of sucrose, and the mixture was sterilized by heating with a plate heater, concentrated into an about 70% syrup, and sterilely bottled to obtain a desired product. Because the product has a mild sweetness and taste, it can be arbitrarily used to sweeten foods for infants, fruits, coffee, cocoa, and tea.

Example B-6

Chewing Gum

Three parts by weight of a gum base was melted by heating to soften the texture, mixed with 6 parts by weight of sucrose, one part by weight of a saccharide powder rich in trehalulose obtained by the method in Example A-4, further mixed with adequate amounts of a flavor and a coloring agent, kneaded by a roll in conventional manner, shaped, and packaged to obtain a desired product which is a chewing gum with a satisfactory texture and taste.

Example B-7

Custard Cream

One hundred parts by weight of corn starch, 100 parts by weight of a high trehalulose content syrup obtained by the method in Example A-3, 80 parts by weight of maltose, 20 parts by weight of sucrose, and one part by weight of salt were sufficiently kneaded, and further mixed with 280 parts by weight of fresh eggs. One thousand parts by weight of boiling milk was gradually added to the mixture and heated while stirring, and the heating was terminated when the contents completely gelatinized to show semi-transparent, cooled, admixed with an adequate amount of a vanilla flavor, weighed, and injected to obtain a desired product having a smooth gloss, mild sweetness, and satisfactory taste.

Example B-8

Uiro-no-moto (premix of sweet rice jelly)

Uiro-no-moto was prepared by mixing 90 parts by weight of rice powder to homogeneity with 20 parts by weight of rice powder, 120 parts by weight of a saccharide powder rich in trehalulose obtained by the method in Example A-4, and 4 parts by weight of pullulan. The product was mixed and kneaded with an adequate amount of matcha and water, and the mixture was placed in a container and steamed for 60 min to obtain an uiro. The uiro has a good biting property, satisfactory taste, and relatively-long shelf life because the retrogradation of starch is well prevented.

Example B-9

Solid Composition for Intubation Nutrient

A solid composition was prepared by mixing 500 parts by weight of a saccharide powder rich in trehalulose obtained by the method in Example A-4, 270 parts by weight of powdered yolk, 209 parts by weight of skim milk, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 part by weigh of vitamin E acetate, and 0.04 part by weight of nicotinic acid amide. Twenty-five g aliquots of the composition were injected into moisture proof small laminated bags, then the bags were heat sealed. One bag of the composition is dissolved in about 150–300 ml water before use and administered to patients orally or administered to their nasal cavity, stomach, and intestines by intubation feeding.

Example B-10

Traumatic Ointment

To 500 parts by weight of a saccharide powder rich in trehalulose, obtained by the method in Example A-4, was added 3 parts by weight of iodine dissolved in 50 parts by weight of methanol, and further admixed with 200 parts by weight of a 10% aqueous pullulan solution to obtain a traumatic ointment with a satisfactory spreadability and adhesiveness. The ointment shortens the healing period and cures the injured surface.

[Effect of the Invention]

As is evident from above, the saccharide compositions, which contain trehalulose obtained by allowing a maltose/trehalose converting enzyme to act on an aqueous sucrose solution, are produced from sucrose in a relatively high yield of trehalulose and readily separated and purified. Trehalulose is a reducing disaccharide consisting of glucose and fructose, and has a high quality and mild sweetness. The saccharide compositions can be administered to humans orally and parenterally and readily metabolized by living bodies without fear of causing toxicity and side effects.

The present saccharide compositions containing trehalulose in the form of a liquid or powder are readily handleable, and have the following properties: Osmosis-controlling ability, filler-imparting ability, gloss-imparting ability, humectancy, viscosity-imparting ability, crystallization-preventing ability, and insubstantial fermentability. These properties can be used advantageously in compositions as a sweetener, taste-improving agent, quality-improving agent, or stabilizer. Thus, the establishment of the present saccharide compositions, their preparation and uses, has a great significance in the food, cosmetic, and pharmaceutical industries.

As is evident from above, the saccharide compositions, which contain trehalulose obtained by allowing a maltose/trehalose converting enzyme to act on an aqueous sucrose solution, are produced from sucrose in a relatively high yield of trehalulose and readily separated and purified. Trehalulose is a reducing disaccharide consisting of glucose and fructose, and has a high quality and mild sweetness. The saccharide compositions can be administered to humans orally and parenterally and readily metabolized by living bodies without fear of causing toxicity and side effects.

The present saccharide compositions containing trehalulose in the form of a liquid or powder are readily handleable, and have the following properties: Osmosis-controlling ability, filler-imparting ability, gloss-imparting ability, humectancy, viscosity-imparting ability, crystallization-preventing ability, and insubstantial fermentability. These properties can be used advantageously in compositions as a sweetener, taste-improving agent, quality-improving agent, or stabilizer. Thus, the establishment of the present saccharide compositions, their preparation and uses, has a great significance in the food, cosmetic, and pharmaceutical industries.

While there has been described what is at present considered to be the preferred embodiments of the invention, it will be understood the various modifications may be made therein, and it is intended to cover in the appended claims all such modifications as fall within the true spirits and scope of the invention.

What is claimed is:

1. A process for producing a saccharide composition containing trehalulose, which comprises allowing a maltose/trehalose converting enzyme to act on a sucrose solution under conditions sufficient to produce said trehalulose, and collecting the resulting trehalulose-containing mixture.

2. The process of claim 1, wherein at least 10 units/g dry solid of said maltose/trehalose converting enzyme is allowed to act on said sucrose solution.

3. The process of claim 1, wherein the concentration of said sucrose solution is at least 0.1 w/v %.

4. The process of claim 1, wherein said enzyme is allowed to act on said sucrose solution in an amount of about 10–1,000 units/g sucrose, on a dry solid basis, at a temperature of below about 80° C. and a pH of about 5.5–9.0 for about 0.1–200 hours.

5. The process of claim 1, wherein said maltose/trehalose converting enzyme is derived from a microorganism.

6. The process of claim 5, wherein said microorganism is selected from microorganisms of the genera Pimelobacter, Pseudomonas, and Thermus.

7. The process of claim 1, which further comprises steps of allowing an invertase to act on the collected trehalulose-containing mixture, and subjecting the resulting mixture to a column chromatography using a strong-acid cation exchange resin to increase the trehalulose content.

8. The process of claim 1, wherein said saccharide composition consists of trehalulose and one or more saccharides selected from the group consisting of fructose, glucose, sucrose, turanose, and palatinose.

9. The process of claim 8, wherein the content of said trehalulose is at least 10 w/w %, on a dry solid basis, and the content of said one or more saccharides is at most 90 w/w %, on a dry solid state.

* * * * *